United States Patent [19]

Sussman

[11] Patent Number: 5,578,082
[45] Date of Patent: Nov. 26, 1996

[54] IOL FOR OPTIMAL CAPSULAR BAG FIT

[75] Inventor: Glenn R. Sussman, Lake Forest, Calif.

[73] Assignee: Allergan, Waco, Tex.

[21] Appl. No.: 250,726

[22] Filed: May 27, 1994

[51] Int. Cl.⁶ ................................................. A61F 2/16
[52] U.S. Cl. ................................................................ 623/6
[58] Field of Search ..................................................... 623/6

[56] References Cited

U.S. PATENT DOCUMENTS

| | | | |
|---|---|---|---|
| Re. 33,039 | 8/1989 | Arnott | 623/6 |
| 4,174,543 | 11/1979 | Kelman | 623/6 |
| 4,268,921 | 5/1981 | Kelman | 623/6 |
| 4,418,431 | 12/1983 | Feaster | 623/6 |
| 4,446,581 | 5/1984 | Blake | 623/6 |
| 4,504,981 | 3/1985 | Walman | 623/6 |
| 4,568,347 | 2/1986 | Reichert, Jr. | 623/6 |
| 4,575,374 | 3/1986 | Anis | 623/6 |
| 4,581,033 | 4/1986 | Callahan | 623/6 |
| 4,585,455 | 4/1986 | Blackmore et al. | 623/6 |
| 4,591,358 | 5/1986 | Kelman | 623/6 |
| 4,608,049 | 8/1986 | Kelman | 623/6 |
| 4,655,775 | 4/1987 | Clasby, III | 623/6 |
| 4,664,665 | 5/1987 | Reuss et al. | 623/6 |
| 4,664,667 | 5/1987 | Kelman | 623/6 |
| 4,676,794 | 6/1987 | Kelman | 623/6 |
| 4,701,181 | 10/1987 | Arnott | 623/6 |
| 4,710,195 | 12/1987 | Giovinazzo | 623/6 |
| 4,725,277 | 2/1988 | Bissonette | 623/6 |
| 4,731,079 | 3/1988 | Stoy | 623/6 |
| 4,816,031 | 3/1989 | Pfoff | 623/6 |
| 4,822,358 | 4/1989 | Jaffe | 623/6 |
| 4,828,558 | 5/1989 | Kelman | 623/6 |
| 4,863,464 | 9/1989 | Dusek | 623/6 |
| 4,863,465 | 9/1989 | Kelman | 623/6 |
| 4,871,363 | 10/1989 | Kelman | 623/6 |
| 4,923,468 | 5/1990 | Wild | 623/6 |
| 4,932,967 | 6/1990 | Kansas | 623/6 |
| 4,990,159 | 2/1991 | Kraff | 623/6 |
| 5,015,254 | 5/1991 | Greite | 623/6 |
| 5,135,540 | 8/1992 | Schepel et al. | 623/6 |
| 5,197,981 | 3/1993 | Southard | 623/6 |

FOREIGN PATENT DOCUMENTS 0125361  11/1984  European Pat. Off. .
2111835  7/1983  United Kingdom .

OTHER PUBLICATIONS

*In search of the ideal IOL, Structural features designed for capsular bag placement*, James A Davison, MD, Ocular Surgery News, Jan. 15, 1992, pp. 55–58.

Primary Examiner—Randy C. Shay
Attorney, Agent, or Firm—Frank J. Uxa

[57] ABSTRACT

An intraocular lens comprising an optic and at least one elongated, resilient fixation member joined to the optic. The fixation member has a proximal segment joined to the optic, a distal segment and an intermediate segment joining the proximal and distal segments. The proximal segment has an inside radius of at least about 0.5 millimeter and a majority of the length of the intermediate segment has an outside radius of no more than about 2 millimeters. The distal segment is substantially longer that either of the proximal or intermediate segments and has an outside radius of between about 4.5 and about 5.5 millimeters.

19 Claims, 2 Drawing Sheets

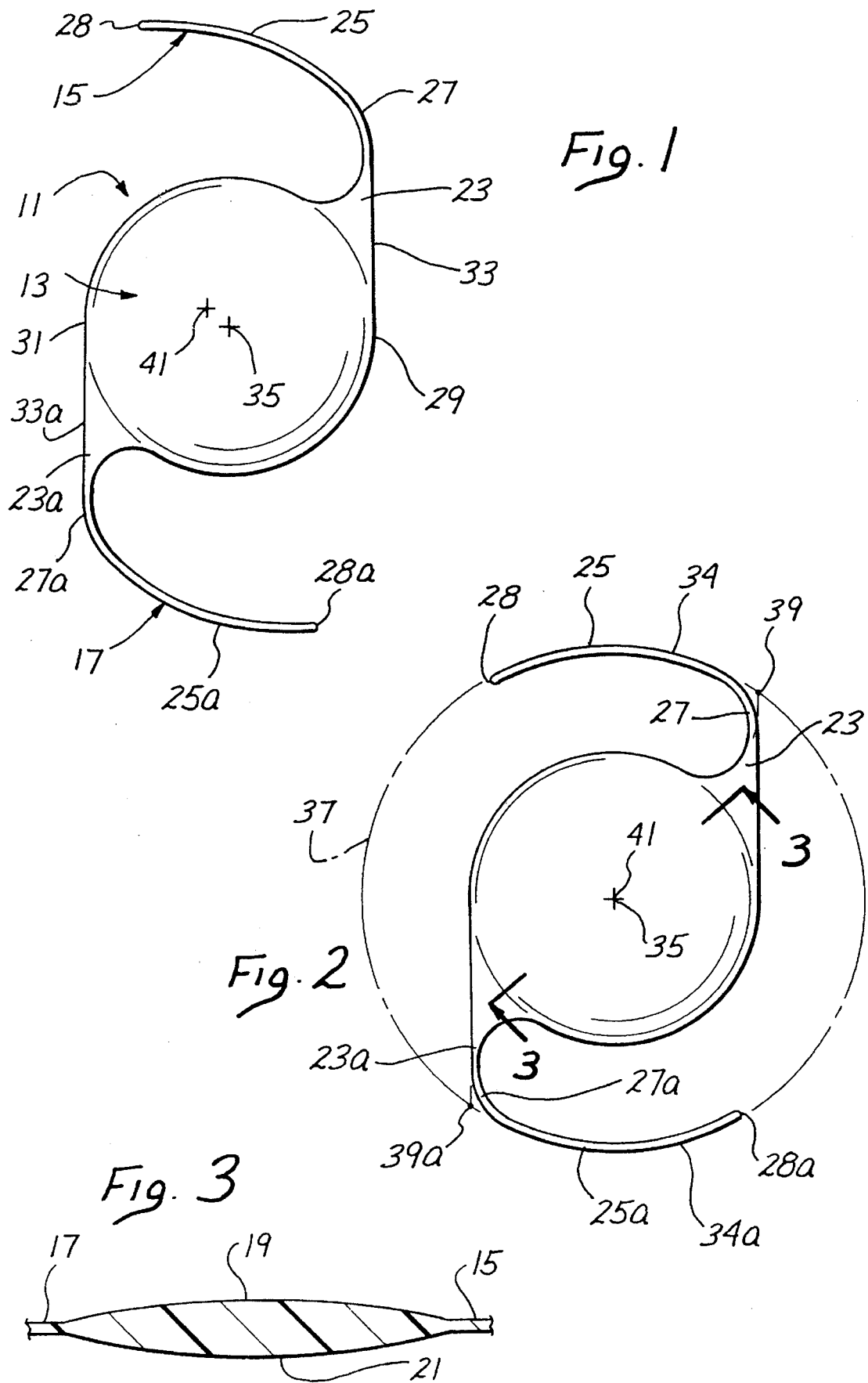

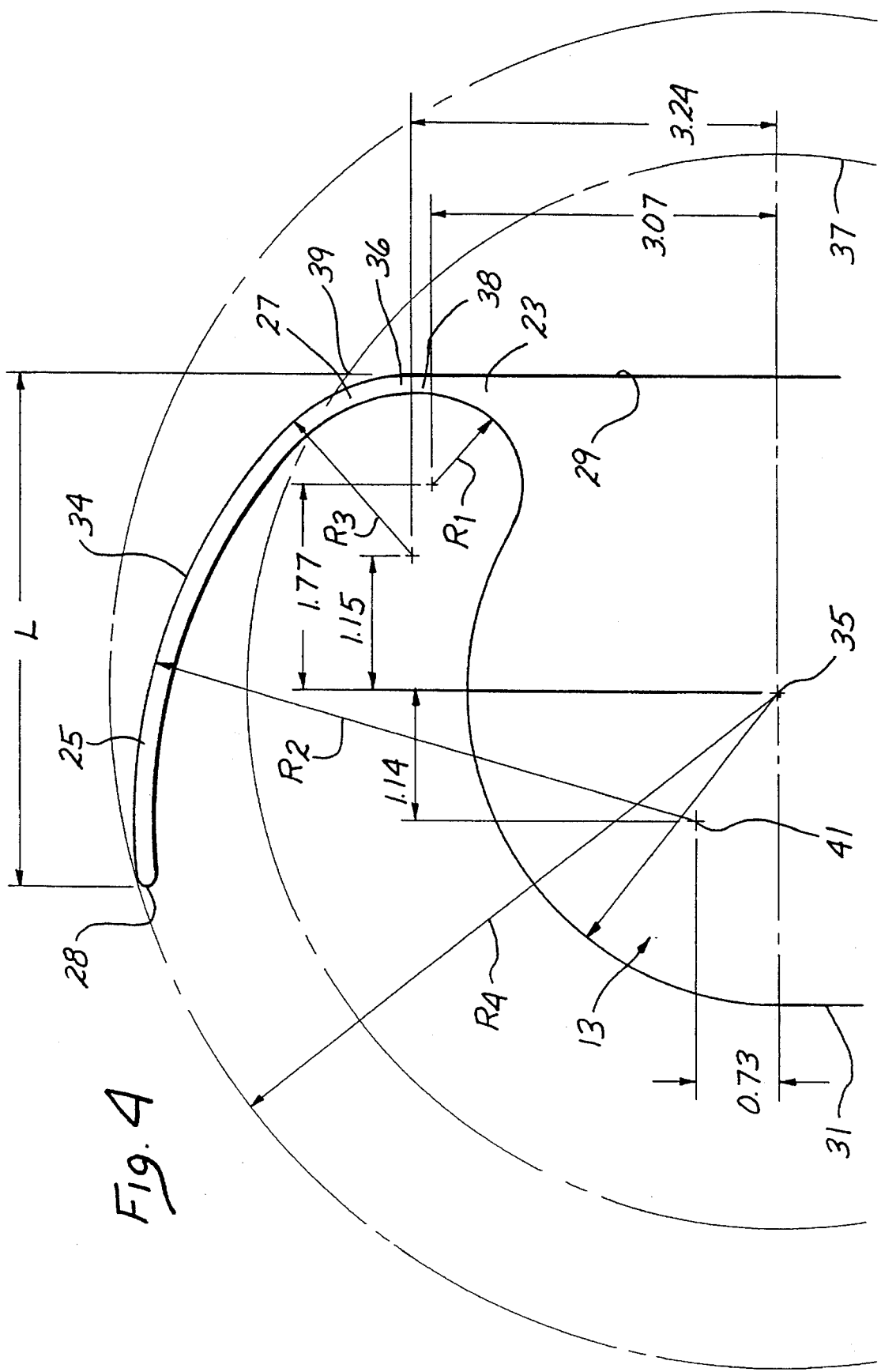

IOL FOR OPTIMAL CAPSULAR BAG FIT

BACKGROUND OF THE INVENTION

This invention relates to an intraocular lens (IOL) and more particularly to an IOL having fixation members which achieve maximum contact with the capsular bag when implanted.

IOL's are a well known type of implant used to replace the natural lens of an eye when the natural lens becomes sufficiently impaired as a result of trauma or disease. An IOL typically includes an optic and at least one fixation member attached to the optic. The fixation member functions to position the optic in correct optical alignment within the eye.

The optic may be constructed of a hard biocompatible polymer, such as polymethylmethacrylate (PMMA). Alternatively, the optic can be constructed from a relatively flexible or deformable material, such as silicone based or acrylic based polymers. When so constructed, the optic can be folded or flexed into a relatively small cross sectional configuration to permit it to be inserted through a relatively small incision into the eye to reduce the trauma and likelihood of infection from the surgery.

Each of the fixation members may be an elongated, resilient strand-like member. Fixation members are constructed of resilient material such as PMMA or polypropylene. In some IOL's, the fixation members are integrally formed with the optic. In other types of IOL's, the fixation members are formed apart from the optic and then attached to the optic.

An IOL can be implanted at different locations within the eye. One common location for implanting of an IOL is the capsular bag.

When an IOL is implanted in the capsular bag, it is desired to achieve a long length of contact between the fixation members and the bag. This reduces unit loading on the bag along the length of the fixation members. When the length of contact between the fixation members and the bag is too short, various problems may result, such as forcing of the bag out of its natural circular shape into an oval shape, stressing the zonules (fibers that attach the bag to the ciliary sulcus), possible irritation or rupture of the zonules and/or the creation of folds in the bag that can disrupt visual acuity and encourage posterior capsule opacification, i.e. the formation of a secondary cataract.

Dusek U.S. Pat. No. 4,863,464 shows an IOL which apparently achieves relatively long contact between the fixation members and the interior structure of the eye. However, these fixation members extend beyond the width of the optic thereby providing an insertion envelope that is larger than the optic, and this is not desirable. Southard U.S. Pat. No. 5,197,981 discloses an IOL which is said to contact more fully and to tension more evenly the capsular bag. However, this construction is made more complex by the requirement that the fixation members have varying cross sectional areas along their lengths. In addition, the fixation members are not configured in a way that is believed to achieve optimal contact with the capsular bag.

SUMMARY OF THE INVENTION

This invention solves these problems by providing an IOL having fixation members which achieve more desirable contact with the capsular bag. This invention achieves a long arc of contact between the fixation members and the capsular bag without requiring an insertion envelope larger than the optic or the complexity of fixation members of varying cross sectional areas along their lengths.

As viewed from the front, the capsular bag is generally circular. The diameter of the capsular bag will be different from patient to patient. For FDA purposes the length of contact between the fixation member and the capsular bag is determined by placing the IOL in a rigid circular well having a diameter of 10 millimeters. For FDA purposes, contact between the fixation member and bag is considered to occur where these members are in contact and where these members are separated by no more than 0.25 millimeter. Thus, for FDA purposes contact between the fixation member and the bag is considered to occur if it would occur anywhere within the annular zone between concentric circles having 9.5 and 10.0 millimeter diameters.

The invention may be embodied in an IOL which includes an optic and at least one elongated, resilient fixation member joined to the optic and extending from the optic. The fixation member may be a separate member suitably mechanically attached to the optic or may be of one piece integral construction with the optic. The optic may be constructed of hard material such as PMMA or of deformable material such as silicone based or acrylic based polymers.

The fixation member has a proximal segment joined to the optic, a distal segment and an intermediate segment between the proximal and distal segments. The proximal segment may have a relatively short inside radius of curvature which is at least about 0.5 millimeter. A shorter inside radius of curvature may cause unacceptable stress concentrations. The distal segment is substantially longer than either of the proximal or intermediate segments and has an outside radius of curvature sized to generally equal the radius of curvature of the capsular bag. This relatively long length and radius of curvature, which is approximately equal to the radius of curvature of the capsular bag, help provide for a long arc in which the radial outer surface of the distal segment contacts the capsular bag. To accomplish this, the outside radius of curvature of the distal segment is preferably between about 4.5 millimeters and about 5.5 millimeters, and more preferably between about 4.75 and 5.25 millimeters.

An important feature of the fixation member configuration is that a majority of the length of the intermediate segment has an outside radius of curvature of no more than about 2 millimeters. This has the advantage of helping to maximize the length of contact with the capsular bag. If the outside radius of curvature exceeds about 2 millimeters the length of contact between the fixation member and the capsular bag is reduced. On the other hand, the outside radius of curvature of the intermediate segment should be at least 0.5 millimeters, because if it is less than that stress concentrations may be unacceptable.

The intermediate segment may be made up entirely of a curved portion, i.e. the portion having the outside radius of curvature referred to above. Alternatively, the intermediate segment may also include a substantially straight portion joining the curved portion to the proximal segment. In this latter event, the curved portion is preferably at least about three times as long as the substantially straight portion and the substantially straight portion is no more than about 0.4 millimeter in length. Thus, the substantially straight portion is very short. Increasing the length of the substantially straight portion may somewhat increase the length of the arc of contact between the fixation member and the capsular bag. However, such lengthening of the straight segment also tends to induce higher stress concentrations at the intermediate segment and also may reduce fixation forces.

The optic has a width and a length perpendicular to the width. To minimize the size of the envelope to be inserted through the incision into the eye, the fixation member extends from the optic such that the fixation member does not extend beyond the width of the optic.

With this invention, it is not necessary that the fixation member be of varying cross sectional area along its length. Preferably, at least a major region of the fixation member is of substantially the same cross sectional area.

To configure the fixation member for optimal capsular bag contact, the fixation member has a free distal end which is no more than about 6.75 millimeters from the optical axis. The fixation member is resiliently deformable radially inwardly to an implanted shape. This provides an arc in the implanted shape of significant length in which the radial outer surface has a radius of between 4.75 and 5.25 millimeters so that it is adapted for contact with the capsular bag along its full length.

It is desirable to keep the fixation member from extending substantially beyond the width of the optic in the implanted shape of the fixation member. On the other hand, it is desired to maximize the length of contact between the fixation member and the capsular bag. Given these constraints, the length of the arc of contact is a function of the width, which may be the diameter, of the optic. Thus, wider optics permit a longer arc of contact than a narrower optic. In addition, the length of the arc of contact is also a function of the overall diameter of the IOL. In a typical case in which the fixation members are diametrically opposed, the overall diameter is the distance between the free ends of the diametrically opposed fixation members when the fixation members are in their normal or relaxed condition. The arc of contact decreases with an increasing overall diameter. Given these constraints, the arc of contact with this invention is maximized and will be at least about 40°. On the other hand, the length of the arc preferably does not exceed about 75 degrees even for an optic of 7 millimeters in diameter and an overall diameter of 11.5 millimeters because a larger arc would extend beyond the width of the optic.

The inside radius of curvature of the proximal segment of the fixation member is preferably no more than about 1.5 millimeters. Generally for radii greater than 1.5 millimeters, a shorter and less desirable radius of curvature of the intermediate segment must be used.

The IOL preferably has a first substantially linear side edge as viewed in plan with such side edge extending along a length dimension of the optic and along an outer surface of the proximal segment. This substantially linear side edge preferably blends into the outside radius of the intermediate segment.

The invention, together with additional features and advantages thereof may best be understood by reference to the following description taken in connection with the accompanying illustrative drawings.

BRIEF DESCRIPTION OF THE DRAWINGS

FIG. 1 is a plan view of one embodiment of an IOL constructed in accordance with the teachings of this invention prior to implantation with the fixation members in a normal or relaxed condition.

FIG. 2 is a plan view of the IOL implanted in a capsular bag with the capsular bag being shown in phantom lines.

FIG. 3 is a sectional view taken generally along line 3—3 of FIG. 2.

FIG. 4, is an enlarged fragmentary plan view illustrating preferred dimensional parameters.

DESCRIPTION OF THE PREFERRED EMBODIMENT

FIG. 1 shows an IOL 11 which includes an optic 13 and identical fixation members 15 and 17. Although the fixation members 15 and 17 could be constructed as separate members and attached to the optic 13 in a known manner, in this embodiment, the optic and fixation members are molded as an integral, one-piece unit. Although the invention is applicable to deformable optics and to optics of different shapes, in this embodiment, the optic 13 is circular, rigid and constructed of PMMA. In this embodiment the fixation members are also constructed of PMMA. The optic 13 is configured to provide the desired diopter correction. In this embodiment, the optic 13 is biconvex (FIG. 3) and has a convex anterior face 19 and convex posterior face 21. Of course, the biconvex configuration of FIG. 3 is purely illustrative.

Because the fixation members 15 and 17 are identical, portions of the fixation member 17 corresponding to portions of the fixation member 15 are designated by corresponding reference numerals followed by the letter "a". The fixation member 15 has a proximal segment 23 joined to the optic 13, a distal segment 25 and an intermediate segment 27 joining the proximal and distal segments. The distal segment is substantially longer than either of the proximal segment 23 or the intermediate segment 27.

A major region of the fixation member 15 is of substantially the same cross sectional area. In this embodiment, the fixation member 15 has the same cross sectional area and configuration throughout the intermediate segment 27 and the distal segment 25, except for a rounded free distal end 28 of the fixation member.

The IOL 11 has first and second substantially linear, parallel, side edges 29 and 31 which extend along a length dimension of the optic 13. The side edge 29 also extends along an outer surface 33 of the proximal segment 23 and the side edge 31 similarly extends along an outer surface 33a of the proximal segment 23a. The optic 13 has a width dimension which is the distance between the side edges 29 and 31 and a length dimension perpendicular to the width. Because the optic 13 is circular, both the length and width dimensions equal the diameter of the optic.

With respect to FIG. 4, the proximal segment 23 has an inside radius of curvature R1 of at least 0.5 millimeter and no more than 1.5 millimeters, and in the form shown in FIG. 5 is about 0.8 millimeter. The distal segment 25 has an outside surface 34 with an outside radius of curvature R2 of between 4.5 and 5.5 millimeters, and in the embodiment shown this outside radius is about 5 millimeters.

An important feature of the invention is that a curved portion 36 of the intermediate segment 27 which forms a majority of the length of the intermediate segment 27 has an outside radius of curvature R3 of no more than about 2 millimeters and no less than about 0.5 millimeter. In the form shown in FIG. 4, the outside radius of curvature R3 of the intermediate segment 27 is about 1.6 millimeters. The outside radius of the intermediate segment blends smoothly into the substantially linear side edge 29.

The intermediate segment 27 also includes a substantially straight portion 38 joining the curved portion 36 to the proximal segment 23. The straight portion 38 is optional and may be eliminated in which event the curved portion 36 would constitute the entire intermediate segment 27 and would merge with the proximal segment 23. The straight side edge 29 forms the outer surface of the straight portion 38 and the inner surface of the straight portion may be either curved or straight. The straight portion 38 is very short and is preferably no more than about 0.4 millimeter in length. The curved portion 36 is at least about three times as long as the straight portion 38. In the embodiment illustrated, the straight portion is only about 0.16 millimeter in length.

The optic 13 has an optical axis 35 which coincides with the geometrical center of the optic 13. The radius of curvature R4, i.e. distance from the optical axis 65 to the distal end 28 is no more than about 6.75 millimeters. Thus, the distance between the distal ends 28 and 28a (FIG. 1) is no more than about 13.5 millimeters. The distance L between an extension of the side edge 29 and the distal end 28 as measured horizontally in this embodiment is about 4.6 millimeters; however this is purely illustrative.

The fixation member 15 does not extend beyond the width of the optic 13. In this regard, the side edge 29 defines the outer surface of the proximal segment 23 and the outside radius of curvature of the intermediate segment 27 blends smoothly into the side edge 29 as shown in FIG. 4. Thus, the width of the optic 13 defines the maximum envelope dimensions for insertion of the optic through an incision into the eye of a patient.

FIGS. 2 and 4 show schematically a circular perimeter 37 of a capsular bag into which the IOL 11 can be inserted. In the implanted condition, the distal segment 25 extends along the perimeter 37. It should be noted that the straight side edge 29 intersects the perimeter 37 at a point 39 and that this point 39 represents the margin of the maximum possible contact area between the fixation member 15 and the perimeter 37 if the fixation member is not to extend beyond the width of the optic 13. It should also be noted that the fixation member 15 is very close to the point 39, and this is one reason why the IOL of this invention achieves a maximum length of contact between the fixation member and the perimeter 37.

The outside radius of curvature R2 of the distal segment 25 has a center 41 in the unstressed condition of the fixation member 15. When the IOL is implanted in the capsular bag as shown in FIG. 2, the fixation member 15 is resiliently deformed radially inwardly such that the outer surface 34 lies along the perimeter 37 of the capsular bag and this shifts the center 41 to the optical axis 35. The primary region of flexure of the fixation member 15 as it is resiliently deformed radially inwardly is adjacent the juncture between the distal segment 25 and the intermediate segment 27. Consequently, by requiring that the outer radius of curvature R2 of the distal segment 25 have a radius of curvature which closely matches the radius of curvature of the typical capsular bag at the perimeter 37, full contact of the distal segment along the perimeter 37 can be achieved. Also, by assuring that the free distal end 28 does not extend beyond an extension of the linear side edge 31, the fixation member 15 will not extend beyond the width of the optic 13 even in the implanted condition.

FIG. 4 also shows by way of example coordinates for locating the center 41 as well as the centers of the applicable radii for the proximal segment 23 and the intermediate segment 27. These dimensions are purely illustrative.

Although an exemplary embodiment of the invention has been shown and described, many changes, modifications and substitutions may be made by one having ordinary skill in the art without necessarily departing from the spirit and scope of this invention.

I claim:

1. An intraocular lens comprising:

an optic having a width and a length perpendicular to the width;

at least one elongated, resilient fixation member extending from the optic such that the at least one fixation member does not extend beyond the width of the optic, said at least one fixation member terminating in a free distal end, a substantial length of said at least one fixation member including the free distal end having a radial outer surface which has a radius of curvature no greater than about 5.5 millimeters;

a proximal segment of said at least one fixation member joined to said optic and an intermediate segment of said fixation member joining the proximal segment to said substantial length, a majority of the length of said at least one fixation member being of substantially uniform cross sectional area;

the optic having an optical axis and the distance from the optical axis to said distal end being no more than about 6.75 millimeters; and said at least one fixation member being resiliently deformable radially inwardly to an implanted shape to provide an arc in which said radial outer surface has a radius of curvature of between about 4.75 and 5.25 millimeters.

2. An intraocular lens as defined in claim 1 wherein the length of said arc with said substantial length resiliently deformed radially inwardly to said implanted shape is not longer than about 75 degrees.

3. An intraocular lens as defined in claim 1 wherein the at least one fixation member does not extend substantially beyond the width of the optic in said implanted shape of the fixation member.

4. An intraocular lens as defined in claim 1 wherein the at least one fixation member has a proximal segment joined to said optic and an intermediate segment joining the proximal segment to said substantial length, a majority of the length of said intermediate segment having an outside radius of no more than about 2.00 millimeters.

5. An intraocular lens comprising:

an optic;

at least one elongated, resilient fixation member joined to the optic and extending from the optic;

said at least one fixation member having a proximal segment joined to the optic, a distal segment and an intermediate segment joining the proximal and distal segments;

said proximal segment having an inside radius of curvature of at least about 0.5 millimeter and no more than about 1.5 millimeters;

a majority of the length of said intermediate segment having an outside radius of curvature of no more than about 2.00 millimeters; and said distal segment being substantially longer than either of said proximal segment or said intermediate segment and having an outside radius of curvature of between about 4.5 millimeters and about 5.5 millimeters.

6. An intraocular lens as defined in claim 5 wherein the intraocular lens has a first substantially linear side edge as viewed in plan, said substantially linear side edge extends along a length dimension of the optic and an outer surface of the proximal segment.

7. An intraocular lens as defined in claim 6 wherein the outside radius of curvature of the intermediate segment blends into said substantially linear side edge.

8. An intraocular lens as defined in claim 6 wherein the intraocular lens has a second substantially linear side edge which is substantially parallel to the first substantially linear side edge and which extends along a length dimension of the optic.

9. An intraocular lens as defined in claim 5 wherein at least a major region of the fixation member is of substantially uniform cross sectional area.

10. An intraocular lens as defined in claim 5 wherein the at least one fixation member extends from the optic such that the at least one fixation member does not extend beyond the width of the optic.

11. An intraocular lens as defined in claim 5 wherein the at least one fixation member is resiliently deformable radially inwardly to an implanted shape to provide an arc in which the outside radius of curvature of said distal segment has a radius of curvature of between about 4.75 and about 5.25 millimeters.

12. An intraocular lens as defined in claim 11 wherein the length of said arc is at least about 40° degrees.

13. An intraocular lens as defined in claim 11 wherein the length of said arc when the distal segment is deformed radially inwardly to said implanted shape is not longer than about 75 degrees.

14. An intraocular lens as defined in claim 11 wherein the at least one fixation member does not extend substantially beyond the width of the optic in said implanted shape of the at least one fixation member.

15. An intraocular lens as defined in claim 5 wherein the intermediate segment includes a curved portion having said outside radius of curvature of the intermediate segment and a substantially straight portion joining the curved portion to the proximal segment.

16. An intraocular lens as defined in claim 15 wherein the curved portion is at least about three times as long as the substantially straight portion.

17. An intraocular lens as defined in claim 15 wherein the substantially straight portion is no more than about 0.4 millimeter in length.

18. An intraocular lens comprising:

an optic;

at least one elongated, resilient fixation member joined to the optic and extending from the optic;

said at least one fixation member having a proximal segment joined to the optic, a distal segment and an intermediate segment joining the proximal and distal segments;

said proximal segment having an inside radius of curvature of at least about 0.5 millimeter;

a majority of the length of said intermediate segment having an outside radius of curvature of no more than about 2.00 millimeters;

said intermediate segment being longer than said proximal segment; and said distal segment being substantially longer than either of said proximal segment or said intermediate segment and having an outside radius of curvature of between about 4.5 millimeters and about 5.5 millimeters.

19. An intraocular lens as defined in claim 18 wherein said inside radius of curvature of the proximal segment is no more than about 1.5 millimeters.

* * * * *

UNITED STATES PATENT AND TRADEMARK OFFICE
CERTIFICATE OF CORRECTION

PATENT NO.   : 5,578,082
DATED        : November 26, 1996
INVENTOR(S)  : Sussman It is certified that error appears in the above-identified patent and that said Letters Patent is hereby corrected as shown below:

Column 7,
Line 7, "the fixation" should read -- the at least on fixation --.

Signed and Sealed this

Sixteenth Day of December, 2003

JAMES E. ROGAN
*Director of the United States Patent and Trademark Office*